United States Patent [19]
Rossi et al.

[11] Patent Number: 4,581,461
[45] Date of Patent: Apr. 8, 1986

[54] MALEATED SILOXANE DERIVATIVES

[75] Inventors: Robert D. Rossi, Levittown, Pa.; Dilip K. Ray-Chaudhuri, Bridgewater, N.J.

[73] Assignee: National Starch and Chemical Corporation, Bridgewater, N.J.

[21] Appl. No.: 483,037

[22] Filed: Apr. 7, 1983

[51] Int. Cl.$^4$ .............................. C07F 7/02; C07F 7/10
[52] U.S. Cl. .................................... 548/406; 556/419; 549/214
[58] Field of Search ....................... 556/419; 549/214; 548/406

[56] References Cited

U.S. PATENT DOCUMENTS 3,576,031  4/1971  Holub et al. ..................... 556/419
3,701,795  10/1972  Holub et al. ..................... 556/419 X
3,808,248  4/1974  Berger et al. ..................... 556/419 X Primary Examiner—Paul F. Shaver
Attorney, Agent, or Firm—Lori D. Tolly; Edwin M. Szala

[57] ABSTRACT

Maleated aminophenoxysiloxanes are prepared by reacting diaminodiphenoxysiloxanes with maleic anhydride. In addition, the resultant maleamic acid derivatives may be cyclized yielding isomaleimide or maleimide siloxane derivatives.

15 Claims, No Drawings

MALEATED SILOXANE DERIVATIVES

BACKGROUND OF THE INVENTION

1. Field of the Invention

This invention relates to novel aminophenoxysiloxane derivatives. More specifically, this invention relates to maleated aminophenoxysiloxanes.

2. Prior Art

Curable adhesive and sealant compositions employing maleimide derivatives are well known in the art. For example, U.S. Pat. No. 3,988,299 (issued Oct. 26, 1976 to B. M. Malofsky) describes the use of small amounts of maleimide derivatives with unsaturated diacrylates in both heat curable and anaerobic curable adhesive compositions. U.S. Pat. No. 4,370,467 (issued Jan. 25, 1983 to M. Gaku et al.) describes the use of maleimides with polyfunctional aromatic cyanate esters in the preparation of curable resin compositions.

The use of bis-maleimides in the synthesis of various polyimides as well as many other polymers including unsaturated hydrocarbon types and polymers containing amino groups is also known. Bis-maleamic acids and bis-maleimides have been used to crosslink natural rubber as well, see J. Am. Chem. Soc., 81, 1187-94 (1959).

N,N'-disubstituted bis-isomaleimides are also known to react with various diamines by free-radical polymerization or condensation polymerization to yield high molecular weight polymaleamides, see J. Polymer Science, 13, 1691-1698 (1975).

Polysiloxanes have also been described as useful in curable adhesive compositions. See U.S. Pat. No. 4,370,358 (issued Jan. 25, 1983 to S. E. Hayes et al.) which describes the use of a radiation curable composition for forming a pressure sensitive silicone adhesive including an epoxy-containing siloxane polymer.

Liquid crystalline elastomers have been made wherein the polymer network includes a polysiloxane main chain. As described in Makromol. Chem., Rapid Commun. 2, 317 (1981), by incorporating the polysiloxane unit, a high degree of flexibility is imparted to the polymer.

The products of the present invention are maleated aminophenoxysiloxane derivatives which contain both siloxane and maleimide or maleamic acid moieties. None of the above references disclose or suggest the products of the present invention.

SUMMARY OF THE INVENTION

According to the present invention, novel maleated aminophenoxysiloxanes and a process for the preparation thereof are herein provided.

The substituted siloxane derivatives of the present invention are represented by formula I

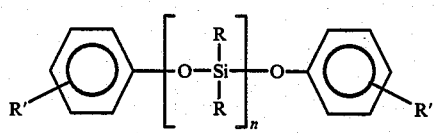

wherein R is independently selected from the group consisting of hydrogen, alkyl of 1 to 3 carbon atoms and phenyl; R' is

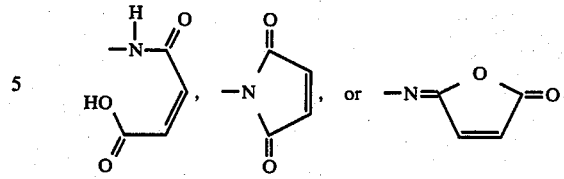

and n=1 to 6. Where n=1 it is understood that the compound is a "silane" rather than a siloxane. However, for purposes of this invention, the siloxane term will include such silane compounds when appropriate as will be apparent to those skilled in the art.

The substituted siloxane derivatives of the present invention are prepared by reacting a diaminodiphenoxysiloxane of formula II

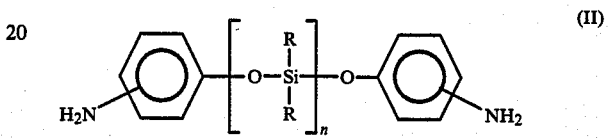

wherein R and n have the meanings given under formula I, with maleic anhydride to produce the diaminodiphenoxysiloxane bis-maleamic acid. The maleamic acid may be further cyclized to yield either the corresponding maleimide or isomaleimide derivative.

PREPARATION OF STARTING MATERIALS

The diaminodiphenoxysiloxane II intermediates used in the present invention are not commercially available; however, the preparation of such materials is known in the literature. See, for example, J. Polymer Sci. 7, 1089-1110 (1969). In providing the diaminodiphenoxysiloxane derivatives of formula II, dialkyldiaminosiloxanes or silanes of formula III

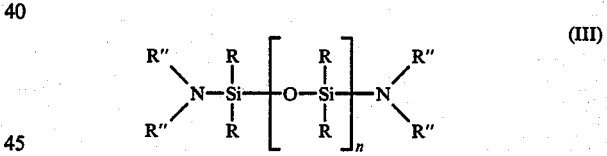

wherein R has the meaning given under formula I; R" is methyl or ethyl; and n=0 to 5 are reacted with aminophenol. The desired orientation of the resultant maleamic acid functionality on the aromatic ring of the siloxane derivative I will determine which aminophenol isomer should be used. Generally, two moles of aminophenol will be reacted with one mole of siloxane or silane of formula III; however, a small excess of aminophenol (about 10 molar percent) may be employed if desired. The reaction is conducted in an inert aromatic solvent such as benzene or toluene under a positive pressure of an inert gas such as argon or nitrogen. In the laboratory, the siloxane or silane of formula III is slowly added over a period of 1-2 hours to the aminophenol in solvent. During addition, the reaction temperature is maintained at about 70°-80° C. After addition is complete, the mixture is heated to reflux temperatures of 70°-100° C. for about 2 hours whereby the aminosilane-phenol condensation reaction proceeds to form the more stable silicon-oxygen bond of the aminophenoxysiloxane derivative while distilling off the dialkylamine by-product as it is formed. The resultant mixture is cooled to temperatures of about 15° C. at which time excess aminophenol may be filtered from the solution. The aminophenoxysiloxane of formula II may then be recovered by distillation of the solvent.

The cited literature reference describes the preparation of 1,3-bis(4-aminophenoxy) tetramethyldisiloxane. The resultant siloxane is further described as being an amber oil. Unexpectedly, by the method of preparation described above and in Example 2, a tan solid (m.p. 56°–57° C.) was obtained.

Dialkyldiaminosiloxanes and silanes of formula III are also not commercially available but can be made from the respective halosiloxanes or halosilanes and dialkylamines by the teachings described in the J. Polymer Science, Vol. 7, reference mentioned above. The halosiloxanes or halosilanes employed are of the general formula IV

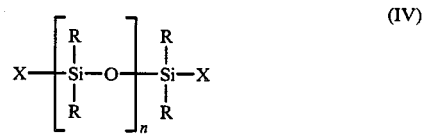

wherein R has the meaning given under formula I; X is a halogen selected from the group consisting of chlorine, bromine, iodine, and fluorine and n=0 to 5. Suitable dialkylamines employed include such short chain amines as dimethylamine and diethylamine. The use of diethylamine is preferred.

In the laboratory, the halosiloxane or halosilane is slowly added over a period of 1–2 hours to an excess amount of dialkylamine in an inert solvent such as ether under anhydrous conditions and a positive pressure of an inert gas such as argon or nitrogen. During addition the reaction temperature is maintained at about 0°–10° C. After the addition is complete, the mixture is then stirred for about 12–16 hours at ambient temperatures. After the aminolysis reaction is complete, the amine hydrochloride byproduct is filtered off and the dialkyldiaminosiloxane or silane of formula III can be recovered by removal of the excess dialkylamine and solvent through distillation.

Halosilanes as well as many of the halosiloxanes of formula IV are commercially available and may be obtained from Petrarch Systems, Inc. Other suitable halosiloxanes commercially unavailable may be prepared by the general teachings of silicon chemistry. For example, tetrachlorosilane or trichlorosilane will react with appropriate Grignard reagents to produce substituted dichlorosilanes. These dichlorosilanes may then undergo partial hydrolysis to yield the desired dichlorosiloxanes.

PREPARATION OF NOVEL MALEATED SILOXANES

According to the present invention, maleation of a siloxane of formula II is achieved by reacting maleic anhydride with the siloxane in a molar concentration of about 2 to 3 moles of maleic anhydride for one mole of the siloxane. The addition reaction is conducted in an inert organic solvent such as acetone, toluene or tetrahydrofuran. The use of acetone is preferred. In the laboratory, a solution of maleic anhydride and solvent is added slowly to a solution of the siloxane and solvent while maintaining the reaction temperature below 10° C. The reaction mixture is stirred for an additional two hours at reduced temperatures after addition to insure completion of the maleation reaction. The resultant bis-maleamic acid derivatives precipitate from solution and may be recovered in good yields by filtration without the need for further purification.

It is noted that siloxanes, in general, are moisture-sensitive and will cleave in the presence of water. Therefore, care must be taken to conduct all reactions involving a siloxane in anhydrous solvents under a positive pressure of an inert gas such as argon or nitrogen. The use of argon is preferred because of its relative high degree of dryness.

The cyclization of maleamic acids to isomaleimides and maleimides is known in the literature. See, for example, U.S. Pat Nos. 4,132,715 and 4,179,444 (issued Jan. 2, 1979 and Dec. 18, 1979 respectively to M. Roth) which describe processes for the manufacture of isomaleimides and maleimides. Maleamic acids may be cyclized in a number of ways to form the corresponding isomaleimides. Various dehydrating agents such as acid anhydrides and acid halides, carbodiimides, and ketene have been used to cyclize maleamic acids at temperatures of about 10°–60° C.

In cyclizing the maleamic acid siloxanes of the present invention, care must be taken when choosing the method of dehydration. Some dehydrating agents were found to cause siloxane cleavage. For example, significant siloxane cleavage occurred when a maleamic acid siloxane of formula I was treated with acetic anhydride and sodium acetate in refluxing acetone at a temperature of about 55° C. The use of N,N'-dicyclohexylcarbodiimide (DCC) in a molar concentration of about two moles of DCC for one mole of maleamic acid siloxane is the preferred dehydrating agent for the cyclization reaction.

Cyclization of the maleamic acids to the corresponding isomaleimides is performed in the presence of an organic solvent which is inert under the reaction conditions. Suitable solvents include various halogenated hydrocarbons, dioxane, and tetrahydrofuran. The preferred solvent of choice is dichloromethane. On a laboratory scale, the cyclization is conducted by adding DCC to a cooled mixture of the maleamic acid siloxane and solvent and stirring at 0°–10° C. for about two hours. The mixture is then stirred at a temperature of 10°–30° C. for about 12–16 hours. Dicyclohexylurea which forms during the reaction can be filtered from the solution and the resultant isomaleimide can then be recovered by distillation of the dichloromethane solvent.

U.S. Pat. No. 4,132,715 (mentioned above) describes the isomerization of isomaleimides to the corresponding maleimides. When in the presence of nucleophilic catalysts such as phenol and triethylamine, isomaleimides rearrange to form maleimides.

It was discovered that when the maleation of aminophenoxysiloxanes of formula II was conducted at temperatures of 45°–50° C., only corresponding maleimide derivatives were later produced by the cyclization procedure described above. It is believed that at such temperatures during maleation, maleic anhydride causes some siloxane cleavage of the aminophenoxysiloxane which results in the production of an amount of maleamic acid of aminophenol. The phenol would be recovered with the diaminodiphenoxysilane bis-maleamic acid derivative during filtration. This nucleophilic impurity would then be present during cyclization, thereby influencing the reaction such that only the maleimide derivative would be formed instead of the expected isomaleimide derivative. It was found that the cyclization reaction produces the isomaleimide derivative first and if a nucleophilic catalyst is present, the isomaleimide derivative rearranges to form the corresponding maleimide with time.

Accordingly, maleimide derivatives of the present invention may be produced by at least two methods. One method involves maleating the siloxanes of formula II at 45°–50° C. and then subsequently cyclizing the respective maleamic acids at temperatures below 10° C. in the presence of nucleophilic impurities which were formed during maleation. A second method of producing the maleimides involves maleating the siloxanes of formula II at temperatures below 10° C. and subsequently cyclizing the respective maleamic acids in the presence of a controlled amount of a nucleophilic catalyst which must be added while employing the same cyclizing reaction conditions. Many suitable nucleophiles may be employed, for instance, phenol, 1-hydroxybenzotriazole, and the maleamic acid of aminophenol. Concentrations of about 40 to 200 mole percent based on maleamic acid are recommended for the complete production of the maleimide, with the preferred amount used being 40–50 mole percent.

The maleated siloxanes of formula I are beige or yellow materials which may be either liquids or solids at room temperature. They are useful as crosslinking agents in adhesive applications when employed in amounts ordinarily used to provide a crosslinkable formulation. These derivatives may be used in other polymeric systems as well.

The following examples will further illustrate the embodiments of the present invention. In the examples, all percentages are given by weight and all temperatures are in degrees Celsius unless otherwise noted.

EXAMPLE 1

Preparation of Bis(diethylamino)-1,1,3,3-Tetramethyldisiloxane

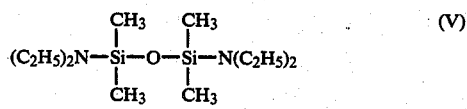

Diethylamine, 184 g. (2.50 mole) of 400 ml. of anhydrous ether were added to a one-liter multi-necked round bottom flask equipped with reflux condenser, pressure equalizing addition funnel, thermometer and stirrer, which was maintained under a positive pressure of argon. The solution was chilled with an ice water bath to 5°–10° C. during the dropwise addition of 100 g. (0.50 mole) of 1,3-dichloro-1,1,3,3,-tetramethyldisiloxane. After addition was completed the mixture was stirred overnight at room temperature (20°–25° C.). The mixture was then filtered and the filtrate was concentrated by rotary evaporation. The resulting residue was distilled at reduced pressure and yielded 81 g. (0.29 mole; 60% theoretical) of V (b.p. 75°–80° C., 2 mm. Hg.).

EXAMPLE 2

Preparation of 1,3-Bis(4-aminophenoxy)-1,1,3,3-Tetramethyldisiloxane

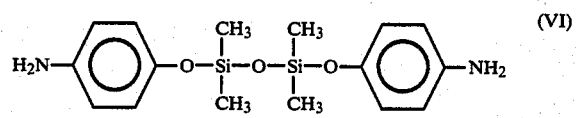

A mixture of 27.3 g. (0.25 mole) of p-aminophenol and 200 ml. of toluene was added to a 500 ml. multi-necked round bottom flask equipped with distillation condenser, pressure equalizing addition funnel, thermometer and stirrer, and was maintained under a positive pressure of argon. The mixture was heated to 70° C. during the dropwise addition of 32.4 g. (0.12 mole) of compound V. After addition was completed, the mixture was heated for 2.5 hours to a temperature where a very slow distillation began. The reaction mixture was cooled to 15° C. and filtered. The filtrate was concentrated on a rotary evaporator to a volume of 75 ml then chilled in a freezer. The diaminodiphenoxysiloxane VI precipitated and was filtered yielding 35.7 g. (0.102 mole; 85% theoretical). Recrystallization of VI from toluene gave a tan solid (m.p. 56°–57° C.).

Analysis for $C_{16}H_{24}N_2O_3Si_2$ (MW=348.56): MW by neutralization equivalent=350.35. Calculated: C, 55.14%; H, 6.94%; N, 8.03%. Found: C, 56.04%; H, 7.05%; N, 7.49%.

EXAMPLE 3

Preparation of 1,3-Bis(4-aminophenoxy)-1,1,3,3-Tetramethyldisiloxane Bis-maleamic Acid

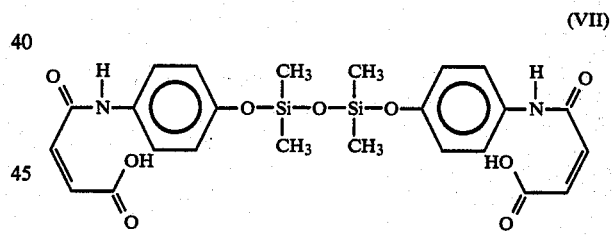

Compound VI, 16.2 g. (0.046 mole) and 100 ml. of acetone were added to a 500 ml. multi-neck round bottom flask equipped with condenser, pressure equalizing additional funnel, thermometer and stirrer, which was maintained under a positive pressure of argon. A solution of 11 g. (0.11 mole) of maleic anhydride in 50 ml of acetone was added dropwise. Upon completion of the addition, the mixture was heated to 45°–50° C. for 2 hours then cooled to 15° C. in an ice bath. The precipitated bismaleamic acid VII was filtered, yielding 12.6 g. (0.023 mole, 50% theoretical). Recrystallization of a small portion of VII gave a yellow crystalline solid (m.p. 177°–180° C.).

Analysis for $C_{24}H_{28}N_2O_9Si_2$ (MW=544): MW by neutralization equivalent=543.9. Calculated: C, 52.94%; H, 5.15%; N, 5.15%; Si, 10.29%. Found: C, 52.63%; H, 5.19%; N, 5.17%; Si, 9.68%.

IR (KBr) 3290 and 3220 $cm^{-1}$ (CONH), 3100 and 1705 $cm^{-1}$ (COOH), 1635 and 1510 $cm^{-1}$ (broad, CONH), 1260 $cm^{-1}$ ($Si(CH_3)_2$) 1065 $cm^{-1}$ (Si—O—Si).

EXAMPLE 4

Preparation of
1,3-Bis(4-aminophenoxy)-1,1,3,3-Tetramethyldisiloxane
Bis-maleimide

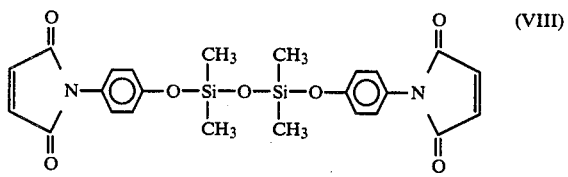
(VIII)

A mixture of 10 g. (0.018 mole) of compound VII and 100 ml. of dry dichloromethane was added to a 250 ml. multi-necked round bottom flask equipped with condenser, thermometer and stirrer, and maintained under a positive pressure of argon. The mixture was cooled to 0°–5° C. with an ice water bath then 7.5 g. (0.036 mole) of N,N'-dicyclohexylcarbodiimide (DCC) was added. The mixture was stirred 2 hours at 5°–10° C. then overnight at room temperature (20°–25° C.). The N,N'-dicyclohexylurea by-product was filtered and washed with dichloromethane. The filtrate and washings were concentrated on a rotary evaporator to yield a yellow oil which was triturated with low boiling petroleum ether to remove unreacted DCC. On further concentration of residual petroleum ether, the product solidified to yield 5.0 g (0.010 mole; 55% theoretical). Recrystallization of VIII from toluene gave a yellow crystalline solid (m.p. 148°–150° C.).

Analysis for $C_{24}H_{24}N_2O_7Si_2$: Calculated: C, 56.67%; H, 4.76%; N, 5.51%; Si, 11.04%. Found: C, 57.09%; H, 4.76%; N, 5.40%; Si, 11.57%.

IR(KBr) 1710 cm$^{-1}$ (C=O), 1255 cm$^{-1}$ (Si(CH$_3$)$_2$), 1080 cm$^{-1}$ (Si—O—Si).

'HNMR (CD$_2$Cl$_2$), δ 0.08 (s, 12H, SiCH$_3$), 7.00 (m, 12H, olefinic and aromatic).

$^{13}$CNMR (CD$_2$Cl$_2$), δ 0.454, 120.704, 125.508, 128.195, 134.469, 154.275, 170.119 ppm.

EXAMPLE 5

Preparation of
1,3-Bis(3-aminophenoxy)-1,1,3,3-Tetramethyldisiloxane
Bis-maleamic Acid

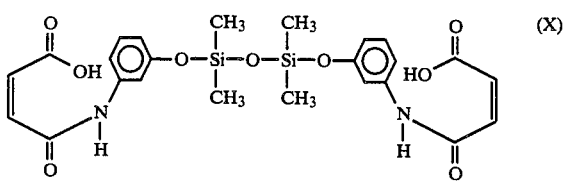
(X)

Using the procedure described in Example 2, 1,3-Bis(3-aminophenoxy)-1,1,3,3-tetramethyldisiloxane (IX) was prepared using m-aminophenol. In a flask equipped as in Example 3, a solution of 16.2 g. (0.046 mole) of IX and 150 ml. acetone was maintained at 5°–10° C. in an ice water bath while a solution of 11 g. (0.11 mole) of maleic anhydride in 50 ml. of acetone was added dropwise. After the addition was completed, the reaction was stirred for an additional 2 hours at 5°–10° C. The precipitated maleamic acid derivative X was filtered yielding 22 g. (0.040 mole, 87% theoretical) of product. Recrystallization of a small portion of the acid from methanol/tetrahydrofuran (95/5) gave a solid (m.p. 162°–164° C.).

Analysis for $C_{24}H_{28}N_2O_9Si_2$ (MW=544): MW by neutralization equivalent=543.7. Calculated: C, 52.9%; H, 5.15%; N, 5.15%; Si, 10.29%. Found: C, 52.95%; H, 5.43%; N, 5.06%; Si, 9.72%.

IR (KBr) 3300 and 3230 cm$^{-1}$ (CONH), 3100 and 1710 cm$^{-1}$ (COOH), 1635, 1575, 1535 amd 1410 cm$^{-1}$ (CONH), 1270 cm$^{-1}$ (Si(CH$_3$)$_2$), 1085 cm$^{-1}$ (Si—O—Si).

$^{13}$CNMR (DMSO-d$_6$), δ 0.648, 111.031, 113.041, 115.057, 129.534, 130.251, 131.742, 139.601, 153.948, 163.168, 166.612 ppm.

EXAMPLE 6

Preparation of
1,3-Bis(3-aminophenoxy)-1,1,3,3-Tetramethyldisiloxane
Bis-isomaleimide

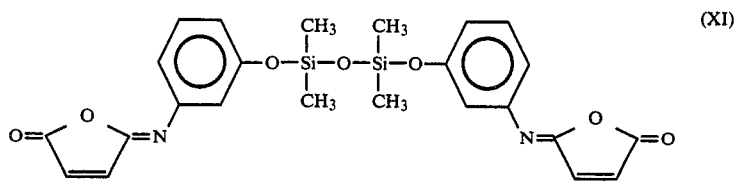
(XI)

The above compound was prepared from Compound X employing the reaction conditions of Example 4. A yellow oil was recovered in 83% yield.

Analysis yielded the following:

IR (Neat) 1805 cm$^{-1}$ (C=O), 1690 cm$^{-1}$ (C=N), 1275 cm$^{-1}$ (Si(CH$_3$)$_2$), 1090 cm$^{-1}$ (Si—O—Si).

'HNMR (CDCl$_3$), δ 0.20 (s, 12H, Si—CH$_3$), 7.10 (complex m, 12H, olefin and aromatic).

$^{13}$CNMR (CDCl$_3$), δ 0.583, 116.548, 118.496, 118.885, 127.913, 129.534, 143.039, 144.468, 150.182, 154.597, 166.934 ppm.

EXAMPLE 7

Preparation of
1,3-Bis(4-aminophenoxy)-1,1,3,3-Tetramethyldisiloxane
Bis-Isomaleimide

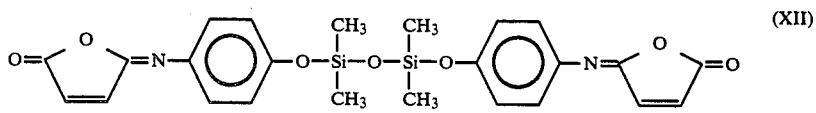
(XII)

1,3-Bis(4-aminophenoxy)-1,1,3,3-tetramethyldisiloxane bis-maleamic acid (VII) was prepared from Compound VI employing the maleation reaction conditions of Example 5. Compound XII was prepared by reacting 10 g. (0.018 mole) of VII with 7.5 g. (0.036 mole) of DCC as described in Example 4. A yellow solid (m.p. 130°-132° C.) was recovered in 100% yield.

Analysis for $C_{24}H_{24}N_2O_7Si_2$: Calculated: C, 56.59%; H, 4.96%, Si, 11.04%. Found: C, 56.83%; H, 4.93%; Si, 10.44%.

IR (KBr) 1795 cm$^{-1}$ (C=O), 1680 cm$^{-1}$ (C=N), 1270 and 800 cm$^{-1}$ (Si(CH$_3$)$_2$), 1080 cm$^{-1}$ (Si—O—Si).

'HHMR (CD$_2$Cl$_2$), δ 0.15 (s, 12H, SiCH$_3$), 7.00 (m, 12H, olefinic and aromatic).

$^{13}$CNMR (CD$_2$Cl$_2$), δ 0.388, 120.641, 127.394, 128.043, 138.105, 143.756, 149.403, 154.338, 167.843 ppm.

EXAMPLE 8

Preparation of
1,5-Bis(diethylamino)-1,1,3,3,5,5-Hexamethyltrisiloxane

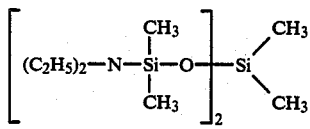
(XIII)

Analogously to the procedure described in Example 1, 159 g. (0.57 mole) of 1,5-dichloro-1,1,3,3,5,5-hexamethyltrisiloxane were reacted with 209.5 g. (2.80 moles) of diethylamine to yield 180 g. (0.51 mole; 89% theoretical) of XIII (b.p. 100-102 C., 2.5 mm Hg).

EXAMPLE 9

Preparation of
1,5-Bis(3-aminophenoxy)-1,1,3,3,5,5-Hexamethyltrisiloxane (XIV)

The above compound was prepared by reacting 20 g. (0.057 mole) of compound XIII with 12.5 g. (0.114 mole) of m-aminophenol in 300 ml. of toluene employing the reaction conditions of Example 2 yielding 24 g. (0.057 mole, crude) of XIV, a near colorless oil.

EXAMPLE 10

Preparation of
1,5-Bis(3-aminophenoxy)-1,1,3,3,5,5-Hexamethyltrisiloxane Bis-maleamic acid (XV)

This compound was prepared analogously to the procedure described in Example 5 with 24 g. of XIV, 11.7 g. (0.12 mole) of maleic anhydride, and 200 ml. of acetone, yielding 24 g. (0.039 mole; 68% theoretical). Recrystallization from cyclohexane/acetone gave a solid (m.p. of 146°-148° C.).

Analysis for $C_{26}H_{34}N_2O_{10}Si_3$ (MW=619): MW by neutralization equivalent=616. Calculated: C, 50.46%; H, 5.53%; N, 4.53%; Si, 13.62%. Found: C, 50.01%; H, 5.33%; N, 4.48%; Si, 12.20%.

IR (KBr) 3290 and 3220 cm$^{-1}$ (CONH), 3100 and 1705 cm$^{-1}$ (COOH), 1635-1500 cm$^{-1}$ (broad, CONH), 1260 and 795 cm$^{-1}$ (Si(CH$_3$)$_2$), 1045 cm$^{-1}$ (Si—O—Si).

EXAMPLE 11

Preparation of
1,5-bis(3-aminophenoxy)-1,1,3,3,5,5-Hexamethyltrisiloxane Bis-isomaleimide (XVI)

A mixture of 20 g. (0.032 mole) of XV and 13.2 g. (0.064 mole) of DCC were reacted in 150 ml. of dichloromethane employing the same reaction conditions of Example 4 yielding 17.5 g. (0.03 mole; 94% theoretical) of a yellow oil.

Analysis yielded the following: IR (Neat) 1800 cm$^{-1}$ (C=O), 1685 cm$^{-1}$ (C=N), 1260 and 800 cm$^{-1}$ (Si(CH$_3$)$_2$), 1070 cm$^{-1}$ (Si—O—Si).

'HNMR (CDCl$_3$), δ 0.03 (s, 6H, SiCH$_3$), 0.11 (s, 12H, SiCH$_3$), 7.00 (m, 12H, olefinic and aromatic).

$^{13}$CNMR (CDCl$_3$), δ 0.648, 0.778, 116.486, 118.303, 118.755, 127.846, 129.404, 142.978, 144.535, 150.120, 154.727, 166.872 ppm.

EXAMPLE 12

This example illustrates the isomerization of 1,3-bis(3-aminophenoxy)-1,1,3,3-tetramethyldisiloxane bis-isomaleimide to the corresponding bis-maleimide in the presence of a nucleophilic catalyst.

To a solution of XI (prepared as in Example 6) and dry dichloromethane at room temperature, was added 40 mole percent of N-(4-hydroxyphenyl)maleimide. The solution was stirred under argon overnight then concentrated by rotary evaporation. IR analysis showed the disappearance of the isomaleimide peaks at 1805 cm$^{-1}$ and 1690 cm$^{-1}$ and the appearance of a strong peak at 1720 cm$^{-1}$ indicative of the normal maleimide.

EXAMPLE 13

This example describes the preparation of 1,3-bis(3-aminophenoxy)-1,1,3,3-tetramethyldisiloxane bis-maleimide from the corresponding bismaleamic acid in the presence of a nucleophilic catalyst.

Following the procedure of Example 4, DCC as well as 40 mole percent of N-(4-hydroxyphenyl) maleamic acid is added to a cooled solution of X (prepared as in Example 5) and dichloromethane. Upon completion of the reaction, the resulting product should be the bis-maleimide.

Summarizing, novel maleated aminophenoxysiloxanes and a process for the preparation thereof are provided diaminodiphenoxysiloxanes are maleated and may be further cyclized to yield maleimide and isomaleimide derivatives.

The preferred embodiments of the present invention having been described above, various modifications and improvements thereon will now become readily apparent to those skilled in the art. Accordingly, the spirit and scope of the present invention is defined not by the foregoing disclosure, but only by the appended claims.

We claim:

1. A compound having the formula:

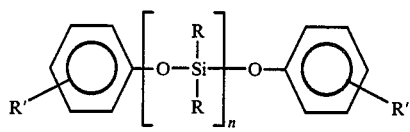

wherein R is independently selected from the group consisting of hydrogen, alkyl of 1 to 3 carbon atoms and phenyl; R' is

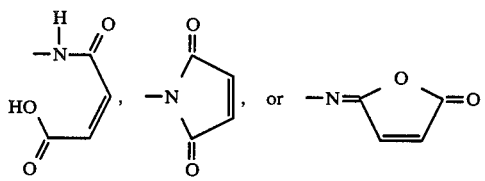

and n=1 to 6.

2. The compound of claim 1, wherein R is methyl, and n is 2 or 3.

3. The compound of claim 1, wherein the compound is 1,3-bis(4-aminophenoxy)-1,1,3,3-tetramethyldisiloxane bis-maleamic acid; 1,3-bis(4-aminophenoxy)-1,1,3,3-tetramethyldisiloxane bis-maleimide; or 1,3-bis(4-aminophenoxy)-1,1,3,3-tetramethyldisiloxane bis-isomaleimide.

4. The compound of claim 1, wherein the compound is 1,3-bis(3-aminophenoxy)-1,1,3,3-tetramethyldisiloxane bis-maleamic acid; 1,3-bis(3-aminophenoxy)-1,1,3,3-tetramethyldisiloxane bis-maleimide; or 1,3-bis(3-aminophenoxy)-1,1,3,3-tetramethyldisiloxane bis-isomaleimide.

5. The compound of claim 1, wherein the compound is 1,5-bis(3-aminophenoxy)-1,1,3,3,5,5-hexamethyltrisiloxane bis-maleamic acid; 1,5-bis(3-aminophenoxy)-1,1,3,3,5,5-hexamethyltrisiloxane bis-maleimide; or 1,5-bis(3-aminophenoxy)-1,1,3,3,5,5-hexamethyltrisiloxane bis-isomaleimide.

6. A process for the preparation of the bis-maleamic acid siloxane of claim 1, wherein R' is

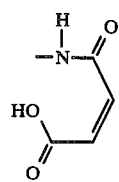

which comprises reacting a diaminodiphenoxysiloxane of the formula

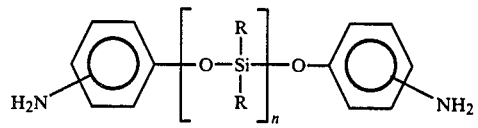

wherein R and n are as defined in claim 1, with maleic anhydride in at least a 1:2 molar ratio in an inert organic solvent at a temperature of 0°-60° C. and recovering the bis-maleamic acid siloxane.

7. The process of claim 6, wherein the inert organic solvent is acetone.

8. A process for the preparation of a bis-maleimide siloxane having the formula

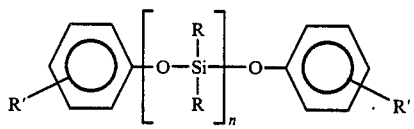

wherein R is independently selected from the group consisting of hydrogen, alkyl of 1 to 3 carbon atoms and phenyl; n=1 to 6; and R' is

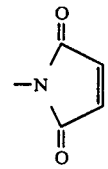

which comprises reacting a diaminodiphenoxysiloxane of the formula

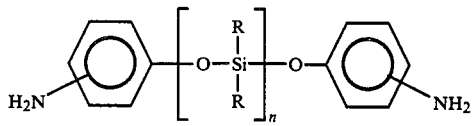

wherein R and n are already defined, with maleic anhydride in at least a 1:2 molar ratio in an inert organic solvent at a temperature of 0°-60° C.; cyclizing the maleated siloxane employing a dehydrating agent at a temperature of 0°-20° C., in the presence of a nucleophilic catalyst which is present as a by-product of the maleation or which has been additionally added; and recovering the bis-maleimide siloxane.

9. The process of claim 8 wherein the dehydrating agent is N,N'-dicyclohexylcarbodiimide.

10. The process of claim 8 wherein the maleation reaction is conducted in acetone, the maleated siloxane is recovered from said acetone and the cyclization reaction is conducted in dichloromethane.

11. The process of claim 8 wherein the nucleophilic catalyst is additionally added in an amount of 40 to 200 weight percent based on the maleated siloxane.

12. A process for the preparation of a bis-isomaleimide siloxane having the formula

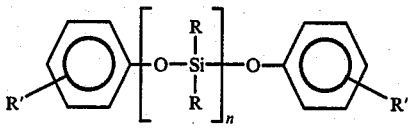

wherein R is independently selected from the group consisting of hydrogen, alkyl of 1 to 3 carbon atoms and phenyl; n=1 to 6; and R' is

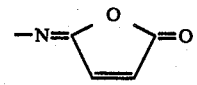

which comprises reacting a diaminodiphenoxysiloxane of the formula

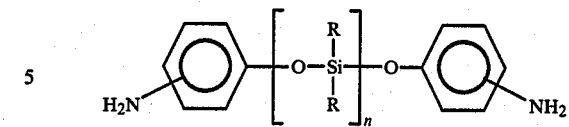

wherein R and n are already defined, with maleic anhydride in at least a 1:2 molar ratio in an inert organic solvent at a temperature of 0°–20° C.; cyclizing the maleated siloxane employing a dehydrating agent at a temperature of 0°–20° C.; and recovering the bis-isomaleimide siloxane.

13. The process of claim 12, wherein the dehydrating agent is N,N'-dicyclohexylcarbodiimide.

14. The process of claim 12, wherein the maleation reaction is conducted in acetone, the maleated siloxane is recovered from said acetone, and the cyclization reaction is conducted in dichloromethane.

15. A process for the isomerization of the bis-isomaleimide siloxane of claim 12 to the corresponding bis-maleimide which comprises isomerizing the bis-isomaleimide in the presence of a nucleophilic catalyst in an inert organic solvent at a temperature of 0°–30° C. and recovering the bis-maleimide siloxane.

* * * * *